United States Patent [19]
Bailey et al.

[11] Patent Number: 4,916,150
[45] Date of Patent: Apr. 10, 1990

[54] 1H-PYRAZOLE-1-ALKANAMINES ANTIARRHYTHMIC COMPOSITIONS AND USE

[75] Inventors: Denis M. Bailey, East Greenbush; Ronald G. Powles, Rotterdam, both of N.Y.

[73] Assignee: Sterling Drug Inc., New York, N.Y.

[21] Appl. No.: 327,228

[22] Filed: Mar. 22, 1989

[51] Int. Cl.$^4$ .................. A61K 31/415; C07D 231/12
[52] U.S. Cl. ..................... 514/406; 514/212; 514/326; 540/603; 546/211; 548/374; 548/378
[58] Field of Search .................. 540/603; 546/211; 548/374, 378; 514/212, 326, 406

[56] References Cited
U.S. PATENT DOCUMENTS 4,072,498  2/1978  Moon et al. ............................ 71/92
4,182,895  1/1980  Bailey .................................. 548/378
4,695,566  9/1987  Heinemann et al. ................. 514/234

OTHER PUBLICATIONS

Ezrin et al., FASEB Journal 2, A1557 (1988).

Primary Examiner—Robert W. Ramsuer
Attorney, Agent, or Firm—Philip E. Hansen; Paul E. Dupont

[57] ABSTRACT

N-[alkylamino)alkyl]-3,4(or 4,5)-diaryl-1H-pyrazole-1-(branched)alkanamides and pyrazole-1-alkanamines useful for treating cardiac arrhythmias in mammals, are prepared by reacting a lower-alkyl ester of pyrazole-1-acetic acid with an appropriate diamine followed by reduction or by reacting the anion of a lower-alkyl ester of a pyrazole-1-acetic acid with an alkylating agent followed by displacement of the ester by an appropriate amine.

11 Claims, No Drawings

1H-PYRAZOLE-1-ALKANAMINES ANTIARRHYTHMIC COMPOSITIONS AND USE

BACKGROUND OF THE INVENTION

1. Field of the Invention

The present invention relates to novel N-[(alkylamino)alkyl]-3,4(or 4,5)-diaryl 1H-pyrazole-1-(branched) alkanamides and pyrazole-1-alkanamines, process for the synthesis of said pyrazole-1-alkanamides, and alkanamines and methods for treating cardiac arrhythmia in mammals utilizing said pyrazole-1-alkanamides and alkanamines.

2. Information Disclosure Statement

U.S. Pat. No. 4,695,566 to Heinemann et. al., discloses as antiarrythmic agents 1H-pyrazol-3-yl(and 1H-pyrazol-5-yl)oxyacetamides of general formula

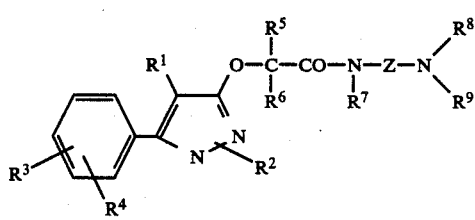

Specifically disclosed are (1) N-[2-(diethylamino)ethyl]-2-[(5-phenyl-1H-pyrazol-3-yl)oxy]acetamide, example 5, and (2) N-[3-(diethylamino)propyl]-2-[(5-phenyl-1H-pyrazol-3-yl)oxy]acetamide, example 24.

U.S. Pat. No. 4,182,895, to Bailey and the related article by Bailey et al. [*J. Med. Chem.* 28, 256–260(1985)] disclose six 1-amino-lower-alkyl-3,4-diphenyl pyrazoles, two of which have antidepressant activity, and three of which have analgesic activity. Also disclosed as an intermediate is "β-[1-(3,4-diphenyl-1H-pyrazolyl)]-N,N-dimethylpropionamide".

Ezrin et al. [FASEB Journal 2, A1557(1988)] describe the antiarrhythmic activity of N-[3-(diethylamino)propyl]-4,5-diphenyl-1H-pyrazole-1-acetamide fumarate.

European patent application No. 299,407, published January 18, 1989 discloses a series of 4,5-diaryl-1H-pyrazole-1-alkanamides as antiarrhythmic agents.

Bondavalli et al. [Farmaco, Ed. Sci. 43, 725–743 (1988)] disclose N-alkyl carbamates of 1-(2-hydroxyethyl)-3,5-diphenyl-1H-pyrazole as antihypertensive, antiarrhythmic, analgesic, antiinflammatory and hypoglycemic agents. Specifically disclosed are the ethyl, isopropyl, phenyl and 1-naphthyl carbamates.

U.S. Pat. No. 4,072,498 to Moon and Kornis discloses a series of pyrazole-1-acetamide herbicides including N,N,α,α-tetramethyl-3,4-diphenylpyrazole-1-acetamide) (example 160), 3-(2-methylphenyl)-and 3-(2-chlorophenyl)-N,N,α,α,tetramethyl-1H-pyrazole-1-acetamide (examples 65 and 66) and 3-phenyl-N,N,α-triethyl-1H-pyrazole-1-acetamide (example 86).

SUMMARY OF THE INVENTION

In a product aspect the invention relates to compounds of the formula I

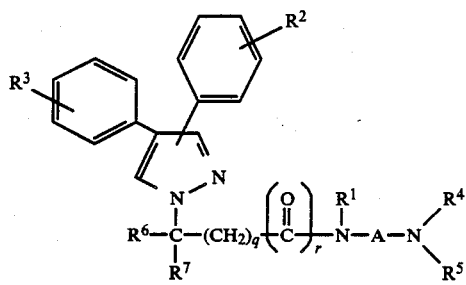

or acid addition salt or solvate thereof wherein $R^1$ is hydrogen or lower-alkyl; $R^2$ and $R^3$ are independently hydrogen, hydroxy, lower-alkyl, lower-alkoxy, or halo; $R^4$ and $R^5$ are independently hydrogen or lower-alkyl, or $R^4$ and $R^5$ together form a straight or branched alkylene chain of four to six carbon atoms; $R^6$ and $R^7$ are independently hydrogen or straight-chain lower-alkyl; r is zero or one; q is one when r is zero; q is zero when r is one and in that case at least one of $R^6$ and $R^7$ is not hydrogen; and A is $CH_2CH(OH)CH_2$ or $(CH_2)_n$ wherein n is an integer from two to eight.

Lower-alkyl as used herein describes linear or branched hydrocarbon chains of four or fewer carbon atoms; lower-alkoxy as used herein describes linear or branched alkyloxy substituents containing four or fewer carbon atoms; halogen describes bromine, chlorine or fluorine.

In a further product aspect, the invention relates to compositions for treating cardiac arrhythmia which comprise compounds of the formula I together with pharmaceutically acceptable excipients or diluents as required.

In a process aspect, the invention relates to a method for treating cardiac arrhythmia in a mammal which comprises adminsitering to said mammal an antiarrythmically effective amount of a compound of formula I.

Processes for preparing a compound of formula I in which r is zero comprise reacting a pyrazole-1-acetate with an amine followed by reduction of the amide carbonyl. Further processes for preparing a compound of formula I in which q is zero and at least one of $R^6$ and $R^7$ is lower-alkyl, comprise reacting the anion of a 3,4 or 4,5-disubstituted pyrazole-1-acetate with an alkylating agent followed by reaction of the ester with an amine.

DETAILED DESCRIPTION INCLUSIVE OF PREFERRED EMBODIMENTS

The synthesis of compounds of the invention may be outlined as shown in scheme A wherein $R^8$ is lower-alkyl.

Scheme A 3,4-diphenyl-1H-pyrazole-1-acetate is desired. A solution of the appropriate diphenylpyrazole and an excess, preferably about a 3-fold excess, of the appropriate α-haloalkanoate, preferably the α-bromoalkanoate, in a suitable solvent is teated with an excess, preferably a 10 to 50% excess, of a suitable base, preferably sodium hydride, at −20° to 100° C., preferably about 25° C. Minor amounts of the 4,5-diphenylpyrazole-1-alkanoates are also formed in the reaction, due apparently to steric effects of $R^6$, and are usually removed by subsequent crystallization or chromatography.

The lower-alkyl ester, III, is reacted with an excess of a primary or secondary amine of formula IV at 20° to 150° C., preferably at 90° to 150° C. When the amine is valuable, the ester III is preferably reacted with about one equivalent of the amine IV in the presence of a tertiary amine, preferably diisopropylethylamine, optionally in an inert solvent.

When products wherein r is zero (Ib) are desired, the appropriate pyrazole-1-alkanamide (Ia) in an inert solvent is reacted with an excess, preferably an 8 to 10-fold molar excess, of a reducing agent such as lithium aluminum hydride or, preferably, diborane at −20° C. to 100° C., preferably at about 65° C.

The compounds of the invention wherein A is $(CH_2)_n$ may also be synthesized as outlined in scheme B.

A lower-alkyl ester, preferably a methyl or ethyl ester of a suitably substituted 3,4 or 4,5-diphenyl-1H-pyrazole-1-acetic acid (II) in a suitable solvent, preferably THF, is treated with a base of sufficient strength to form the carbanion at the α-carbon, preferably lithium diisopropylamide, at −78° to 20° C., preferably at −78° C. A compound consisting of the alkyl group $R^7$ attached to a group X that is subject to nucleophilic displacement (X=Cl, Br, I, or sulfonate) preferably the alkyl iodide, is added and the α-alkylated product, III, is formed. If a second α-alkyl group is desired (i.e. $R^6$ and $R^7$ both lower-alkyl) the process may be repeated.

Alternatively the compound II where $R^6$ is lower-alkyl or compound III where $R^7$ is hydrogen may be synthesized from a known 3,4-diphenyl-1H-pyrazole by alkylation with an α-haloalkanoate when the α-alkyl

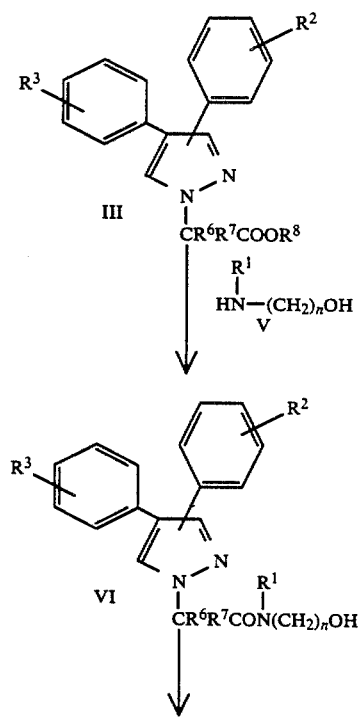

Scheme B

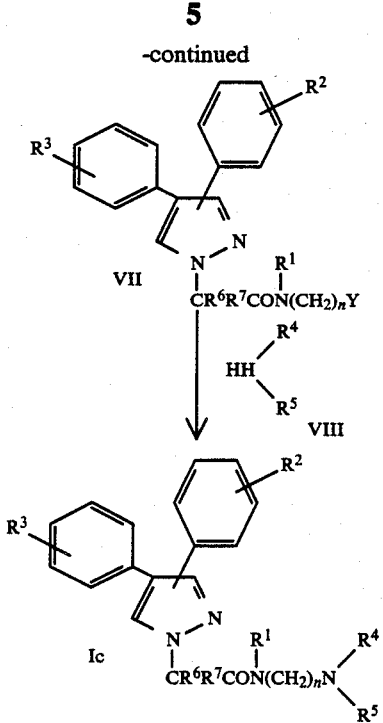

A lower-alkyl ester, preferably a methyl or ethyl ester of a suitably substituted 3,4- or 4,5-diphenyl-1H-pyrazole-1-alkanoic acid III is reacted with an excess of a primary or secondary -aminoalkanol V optionally in the presence of a base/solvent such as pyridine at $-20°$ to $20°$ C., preferably at $90°-100°$ C. to produce an N-[-hydroxylakyl]pyrazole-1-alkanamide of formula VI. The hydroxyalkylalkanamide VI is activated preferably by sulfonylation, preferably with methanesulfonyl chloride, in the presence of a base/solvent such as pyridine at $-20°$ to $20°$ C., preferably at $0°$ C., to produce an alkylalkanamide of formula VII wherein Y is a group which is subject to nucleophilic displacement such as toluenesulfonate or methanesulfonate.

Alternatively, the hydroxyalkylalkanamide VI is converted to the corresponding halide VII, (Y=Cl, Br or I) by phosphorus trihalide, phosphorus pentahalide, thionyl halide or tetrahalomethane with trialkylphosphine. The group Y is then displaced by reaction in the presence or absence of solvent with an appropriate primary or secondary amine VIII at $20°$ to $100°$ C.

The ester III may be synthesized from the appropriately substituted desoxybenzoin by formylation by means of known procedures [Russel et al J. Am. Chem. Soc. 76, 5714(1954)] followed by condensation with a hydrazinoacetic acid ester in a suitable solvent, preferably ethanol, at $20°$ to $100°$ C., preferably at $25°$ C. The hydrazinoacetate is preferably used in the form of a mineral acid salt from which the free hydrazine is liberated in situ by the addition of about one equivalent of a base, preferably pyridine.

When only the 4,5-diphenyl isomer of the products of formula I is desired, the 4,5-diphenyl ester III may be synthesized from the appropriately substituted desoxybenzoin by a two-step procedure comprising reaction with N,N-dimethylformamide dimethyl acetal in an inert solvent, preferably methyl tert-butyl ether, at $20°-100°$ C. preferably at about $55°$ C., followed by cyclization with a lower-alkyl ester of hydrazinoacetic acid as described above.

The compounds of formulas Ia and Ib are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedure.

The structures of the compounds of the invention were established by the mode of synthesis, by elemental analysis, and by infrared, ultraviolet and nuclear magnetic resonance spectroscopy. The course of the reactions and the identity and homogeneity of the products were assessed by thin layer chromatography (TLC) or gas-liquid chromatography (GLC). The starting materials are either commercially available or may be prepared by procedures well known in the art.

In the following procedures melting points are given in degrees C. and are uncorrected. The abbreviation THF stands for tetrahydrofuran, DMF stands for N,N-dimethylformamide and Ac stands for acetyl residue, $CH_3CO$.

EXAMPLE 1A

Ethyl 4,5-diphenyl-1H-pyrazole-1-acetate

A slurry of 200 g (0.89 mol) of formyldesoxybenzoin and 138 g (0.89 mol) of ethyl hydrazinoacetate hydrochloride in 2 L of ethanol were stirred at room temperature and 72 mL (0.89 mol) of pyridine was added dropwise. The reaction was stirred at room temperature and progress was assessed by periodic TLC using 3% acetic acid, 25% acetone and 72% toluene on silica gel. When, after the addition of a further 3 mL of pyridine over the course of 18 hours, the reaction was judged complete by TLC, the solvent was stripped in vacuo and the residue slurried in ethyl acetate. The ethyl acetate solution was filtered free of solid impurity, washed with water then saturated sodium chloride solution and dried over magnesium sulfate. The ethyl acetate was stripped to a reddish oil which was triturated in pentane to yield 156 g of solid. The product was recrystallized carefully from ether-pentane to yield 44.6 g of ethyl 4,5-diphenyl-1H-pyrazole-1-acetate, mp 79°–81° C. By repeated careful crystallization from ether-pentane a further 99.6 g of the 4,5-diphenyl isomer may be obtained for a total yield of 144.2 g (53% yield).

EXAMPLE 1B

Ethyl 4,5-Diphenyl-1H-pyrazole-1-acetate

When only the 4,5-diphenyl isomer is desired the following procedure is preferred. A mixture of 778 g (3.96 mol) deoxybenzoin, 580 mL (4.38 mol) of N,N-dimethylformamide dimethyl acetal, and 775 mL of methyl tert-butyl ether was refluxed for 3 hours. The reaction mixture was cooled on ice to 0°–5° C. The precipitated solid was collected by filtration, the filter cake washed with 250 mL of cold methyl tert-butyl ether twice and dried in vacuum chamber at 65° C. to afford 913 g (92%) of 3-(dimethylamino)-1,2-diphenyl-2-propen-1-one, mp 128°–133° C. A slurry of 913 g (3.64 mol) of 3-(dimethylamino)-1,2-diphenyl-2-propen-1-one in 3.4 L of absolute ethanol was treated with 618 g (4 mol) of ethyl hydrazinoacetate hydrochloride in one portion. The mixture was stirred at room temperature for 1 hour, filtered through diatomaceous earth, and the filtrate treated with 7 L of 50% aqueous ethanol with stirring. Cooling of the resultant solution to 0°–5° C. provided a white solid which was collected by filtration, washed with 250 mL of cold 50% ethanol twice and dried in vaccum at 40° C. to provide 970 g (87%) of ethyl 4,5-diphenyl-1H-pyrazole-1-acetate, mp 76°–80° C., containing none of the 3,4-diphenyl isomer detectable by GLC.

EXAMPLE 2

Ethyl 3,4-diphenyl-1H-pyrazole-1-acetate

Chromatography of the mother liquors from Example 1A on silica gel using 1:1 chloroform-hexane provided up to 20% of the 3,4-diphenyl isomer. The 3,4-diphenyl isomer (Example 2) may be distinguished from the 4,5-diphenyl isomer (Example 1) by its higher Rf on TLC. An analytical sample may be obtained by distillation at 0.2 mm, boiling range 186°–189° C.

EXAMPLE 3

Ethyl 4,5-bis(4-fluorophenyl)-1H-pyrazole-1-acetate and ethyl 3,4-bis(4-fluorophenyl)-1H-pyrazole-1-acetate Following the procedure of Example 1, 19.7 g (0.076 mol) of 1,2-bis(4-fluorophenyl)-3-hydroxy-2-propen-1-one, 11.8 g (0.076 mol) of ethyl hydrazinoacetate hydrochloride and 6.3 mL (0.078 mol) of pyridine were reacted at room temperature to produce 19.9 g of the mixed 4,5- and 3,4-diphenyl isomers. The isomers were separated by high pressure liquid chromatography on silica gel eluting with 97% toluene, 3% ethyl acetate. The peak with k'=2.0 yielded 1.8 g of the 3,4-diphenyl isomer, mp 98°–99° C., and the peak with k'=4.0 yielded 11.16 g of the 4,5-diphenyl isomer, mp 83°–84° C.

EXAMPLE 4

Ethyl 4-(4-methoxyphenyl)-5-phenyl-1H-pyrazole-1-acetate

Following the procedure of example 1B 11 g (0.39 mol) of 3-(dimethylamino)-2-(4-methoxyphenyl)-1-phenyl-2-propen-1-one and 6.6 g (0.43 mol) of ethyl hydrazinoacetate hydrochloride were reacted in 55 mL of absolute methanol under nitrogen. After 1½ hours, 11.2 g of solid product was filtered off, mp 81°–84° C.

EXAMPLE 5

Ethyl 5-(4-hydroxyphenyl)-4-phenyl-1H-pyrazole-1-acetate

Following the procedure of example 1B, 15 g (0.05 mol) of 3-(dimethylamino)-1-(4-hydroxyphenyl)-2-phenyl-2-propene-1-one and 9 g (0.058 mol) of ethyl hydrazino acetate hydrochloride were reacted in 75 mL of absolute ethanol. After 1½ hours, 14.38 g of solid product was filtered off, mp 130°–135° C.

EXAMPLE 6

Ethyl 4-(4-fluorophenyl)-5-phenyl-1H-pyrazole-1-acetate

Following the procedure of example 1B, 13.8 g (0.0645 mol) of 2-(4-fluorophenyl)-1-phenylethanone was reacted with 20 mL of dimethyl formamide dimethyl acetal to yield 13.6 g of 3-(dimethylamino)-2-(4-fluorophenyl)-1-phenyl-2-propen-1-one, mp 115°–116° from isopropyl acetate. The enamine (10.5 g, 0.039 mol) was reacted with 6.03 g (0.039 mol) of ethyl hydrazinoacetate hydrochloride to yield 12.1 g of product mp 86°–87° C. from methyl-t-butyl ether.

EXAMPLE 7

Ethyl 4-(4-chlorophenyl)-5-phenyl-1H-pyrazole-1-acetate

By a procedure analogous to that of example 6, 8.5 g of ethyl 4-(4-chlorophenyl)-5-phenyl-1H-pyrazole-1-acetate mp 75°–76° from triethylamine, was synthesized from 11.48 g (0.049 mol) of 2-(4-chlorophenyl)-1-phenylethanone, 12 mL of dimethylformamide dimethyl acetal and 4.95 g (0.032 mol) of ethyl hydrazinoacetate hydrochloride.

EXAMPLE 8

Ethyl 4,5-diphenyl-α-methyl-1H-pyrazole-1-acetate

A solution of lithium diisopropylamide was prepared by adding at −15° C. under nitrogen (0.108 mol) of diisopropyl amine to 43.5 mL (0.108 mol) of 2.5M n-butyllithium in hexane that had been diluted with 200 mL THF. A solution of 30 g (0.098 mol) of ethyl 4,5-diphenyl-1H-pyrazole-1-acetate of example 1 in 300 mL of THF was cooled to −78° C. and the solution of diisopropylamide was added under nitrogen. The reaction was stirred 1 hr at −78° C., 30 mL (0.049 mol) of methyl iodide was added, and the stirring was continued 30 minutes at −78° C. before allowing the reaction to come to room temperature. The reaction was quenched with 30 mL of saturated aqueous ammonium chloride and the solvent was stripped. The residue was dissolved in ethyl acetate, washed with water, dried, stripped and put through a silica gel column with a gradient of 5% to 50% ethyl acetate in hexane. The product was obtained as 27 g of an oil which could be crystallized, if desired, from ethyl acetate-hexane.

EXAMPLE 9

Ethyl 3,4-Diphenyl-α-methyl-1H-pyrazole-1-acetate

A. A solution of 45.2 g (0.205 mol) of 3,4-(4,5)-diphenylpyrazole and 80 mL (0.616 mol) of ethyl 2-bromopropionate in DMF at room temperature was treated with 13.8 g (0.37 mol) of a 60% dispersion of sodium hydride in mineral oil. The mixture was stirred 3 days, poured into water, extracted into ethyl acetate, stripped, and put through a silica gel column using a gradient from 2% to 5% ethyl acetate in hexane. After stripping solvent, the fractions containing the slower-running of the two major components yielded 27.8 g of ethyl 3,4-diphenyl-α-methyl-1H-pyrazole-1-acetate as an oil containing about 11% of the 4,5-isomer.

B. By a procedure substantially similar to that of example 8, it is contemplated that ethyl 3,4-diphenyl-α-methyl-1H-pyrazole-1-acetate may be synthesized from ethyl 3,4-diphenyl-1H-pyrazole-1-acetate of example 2 and methyl iodide.

EXAMPLE 10

Ethyl α,α-dimethyl-4,5-diphenyl-1H-pyrazole-1-acetate

By a procedure substantilly similar to that of example 8, it is contemplated that ethyl α,α-dimethyl-4,5-diphenyl-1H-pyrazole-1-acetate may be synthesized from ethyl 4,5-diphenyl-α-methyl-1-H-pyrazole-1-acetate of example 8 and methyl iodide.

EXAMPLE 11

Ethyl-4-(4-methoxyphenyl)-5-phenyl-1H-pyrazole-1-acetate

By a procedure substantially similar to that of example 8, it is contemplated that ethyl-4-(4-methoxyphenyl)-5-phenyl-1H-pyrazole-1-acetate may be synthesized from ethyl 4-(4-methoxyphenyl)-5-phenyl-1H-pyrazole-1-acetate of example 4 and ethyl iodide.

EXAMPLE 12

N-[3-(diethylamino)propyl]-4,5-diphenyl-1H-pyrazole-1-acetamide hemihydrate

A. A mixture of 8 g (0.026 mol) of ethyl 4,5-diphenyl-1H-pyrazole-1-acetate of example 1 and 40 mL (0.25 mol) of diethylaminopropylamine was heated on a steam bath under nitrogen for 14 hours. The excess diethylaminopropylamine was stripped in vacuo and the residue dissolved in ether. The ether solution was washed two times with water, once with saturated sodium chloride, dried over magnesium sulfate, filtered and evaporated in vacuo. The resulting white residue was dissolved in ether and a small amount of undesired material was removed by filtration after addition of some pentane. The filtrate was stripped, redissolved in ether, dried over magnesium sulfate, treated with decolorizing carbon, filtered and evaporated. The resulting residue was triturated in water filtered and rinsed with water to yield 8.55 g (82%) of N-[3-(diethylamino)propyl]-4,5-diphenyl-1H-pyrazole-1-acetamide hemihydrate, mp 70°-74° C. The product can be recrystallized from wet ether.

B. The methane sulfonate salt was prepared by dissolving 6 g of the free base in 150 mL of isopropyl alcohol and treating with one equivalent of methanesulfonic acid; mp 166°-168° C.

C. The fumarate salt was prepared by dissolving 70 g of the free base in 250 mL of hot isopropyl alcohol, adding 20.8 g of fumaric acid in 100 mL of methanol, refluxing, filtering, and cooling. There was obtained 83 g of N-[3-(diethylamino)propyl]-4,5-diphenyl-1H-pyrazole-1-acetamide (E)-2-butenedioate (1:1), mp 154°-156° C.

For large scale preparation of N-[3-(diethylamino)propyl]-4,5-diphenyl-1H-pyrazole-1-acetamide (E)-2-butenedioate (1:1) the following procedure was found to be superior: A solution of 2.2 kg (7.3 mol) of ethyl 4,5-diphenyl-1H-pyrazole-1-acetate in 4.3 kg (33 mol) of 3-diethylaminopropylamine was heated at 135°-148° C. for 1.5 hours while distilling off ethanol. Excess amine was removed by vacuum distillation; the residue was dissolved in 6 L of isopropyl acetate and washed twice with 3 L of water. The organic layer was concentrated to a white solid, which was dissolved in 14 L of ethanol, treated with 0.96 kg (8.3 mol) of fumaric acid, and heated to 75° C. to achieve a clear solution. The solid product was obtained by filtration of the cooled solution. The first crop weighed 3.1 kg (84% yield) and melted at 157°-159° C.; a second crop, m.p. 155°-157° C., 0.36 kg (9%) was obtained upon concentration of the mother liquors.

D. The toluenesulfonate salt was prepared by dissolving 70 g of the free base in 250 mL of hot isopropyl alcohol, treating with 34 g of p-toluenesulphonic acid monohydrate in 100 mL of isopropyl alcohol, filtering and cooling. There was obtained 96.8 g of the toluenesulfonate salt, mp 126°-129° C.

E. The maleate salt was prepared by dissolving 70 g the free base in 250 mL of isopropyl and 1 L of isopropyl acetate, adding 20.8 g of maleic acid, refluxing, cooling and stripping. The resulting residue was suspended in about 600 mL of ethyl acetate and 12.8 mL of water was added with vigorous stirring. The resulting solid was filtered off and recrystallized from 300 mL of water to yield 58.9 g of N-[3-(diethylamino)propyl]-4,5-diphenyl-1H-pyrazole-1-acetamide (Z)-2-butenedioate (1:1) sesquihydrate, mp 70°-71° C.

EXAMPLE 13

N-[3-(Dimethylamino)propyl]-4,5-diphenyl-1-H-pyrazole-1-acetamide monohydrochloride hemihydrate A mixture of 86.5 g (0.28 mol) of ethyl 4,5-diphenyl-1H-pyrazole-1-acetate of Example 1 and 340 mL (2.8 mol) of dimethylaminopropylamine was stirred on a steam bath under nitrogen for 18 hours. The excess dimethylaminopropylamine was stirred in vacuo, the residue was dissolved in 700 mL of ether and washed two times with water. On washing with saturated sodium chloride solution, the ether layer solidified. The resulting was filtered off and dissolved in dichloromethane, washed with saturated sodium chloride solution, and stripped. The residue was slurried in water and the solid product filtered off. After thorough drying, it was dissolved in 700 mL of absolute ethanol, treated with a slight excess of ethanolic HCl, filtered free of some undesired solids, and stripped. The residue was recrystallized from about 800 mL of ethanol by chilling to yield 79 g of the hydrochloride ethanol solvate, mp 101°-104° C., which showed a single spot on TLC on silica gel with 5% isopropyl amine in chloroform as eluant. The ethanol solvate was dissolved in about 800 mL of warm isopropyl alcohol and stripped; the process was repeated and the resulting residue was crystallized from about 350 mL of wet THF by recycling the mother liquor several times to yield 26.2 g of N-[3-(dimethylamino)propyl]-4,5-diphenyl-1H-pyrazole-1-acetamide monohydrochloride hemihydrate, mp 118°-121° C.

EXAMPLE 14

N-[2-(Dimethylamino)ethyl]-4,5-diphenyl-1H-pyrazole-1-acetamide hemihydrate

A mixture of 9 g (0.029 mol) of ethyl 4,5-diphenyl-1H-pyrazole-1-acetate of Example 1 and 31 mL (0.29 mol) of dimethylaminoethylamine was stirred on a steam bath under nitrogen for 18 hours. The excess dimethylamino ethylamine was stripped in vacuo, the residue dissolved in 300 mL of ether, treated with decolorizing carbon, filtered, and stripped to approximately 10 g of residue. This was triturated in water, filtered, washed and recrystallized from ether to yield 7.16 g of N-[2-(dimethylamino)ethyl]-4,5-diphenyl-1H-pyrazole-1-acetamide hemihydrate, mp 85°-88° C.

EXAMPLE 15

N-[6-(Dimethylamino)hexyl]-4,5-diphenyl-1H-pyrazole-1-acetamide

A mixture of 8 g (0.026 mol) of ethyl 4,5-diphenyl-1H-pyrazole-1-acetate of Example 1, 4.1 g (0.028 mol) of dimethylaminohexylamine and 33.3 mL (0.19 mol) of diisopropylethylamine was stirred on a steam bath under nitrogen for 18 hours. Thin layer chromatography on silica gel with 5% isopropylamine in chloroform showed incomplete reaction. Another 1 mL of dimethylaminohexylamine was added and stirring continued on a steam bath for an additional 24 hours. The reaction was stripped in vacuo, taken up in 200 mL of ether, washed two times with water, washed once with half saturated sodium bicarbonate solution, washed with water again, washed with saturated sodium chloride solution, dried over magnesium sulfate, treated with decolorizing carbon, filtered and stripped. The residue was taken up in ether and treated with a slight excess of hydrochloric acid. The hydrochloride salt was extracted into water and washed three times with ether; the water layer was chilled, and made basic with solid sodium carbonate and extracted two times with ether. The ether extracts were combined, washed once with saturated sodium chloride, dried over magnesium sulfate, treated with decolorizing carbon, filtered and stripped. The resulting residue was triturated in pentane to yield 4.14 g of N([6-(dimethylamino)hexyl]-4,5-diphenyl-1H-pyrazole-1-acetamide, mp 60°-63° C.

EXAMPLE 16

N-[4-(Dimethylamino)butyl]-4,5-diphenyl-1H-pyrazole-1-acetamide

By a procedure substantially similar to that of Example 15, 3.91 g of N-[4-(dimethylamino)butyl]-4,5-diphenyl-1H-pyrazole-1-acetamide, mp 77°-79° C., was synthesized from 8 g (0.026 mol) of ethyl 4,5-diphenyl-1H-pyrazole-1-acetate, 3.4 g of dimethylaminobutylamine (0.029 mol) and 33.3 mL (0.18 mol) of diisopropylethylamine.

EXAMPLE 17

N-[2-(Diethylamino)ethyl1-4,5-diphenyl-1H-pyrazole-1-acetamide

By a procedure involving reaction conditions substantially similar to those of Example 14 and a workup substantially similar to that of Example 12, 6.46 g of N-[2-(diethylamino)ethyl]-4,5-diphenyl-1H-pyrazole-1-acetamide, mp 67°-69° C., was synthesized from 10 g of ethyl 4,5-diphenyl-1H-pyrazole-1-acetate and 46.4 mL of N,N-diethylethylenediamine. The product was recrystallized from ether.

EXAMPLE 18

4,5-Diphenyl-N-[2-(1-piperidinly)ethyl]-1H-pyrazole-1-acetamide

By a procedure substantially similar to that of Example 15, 10.57 g of 4,5-diphenyl-N-[2-(1-piperidinyl)-ethyl]-1H-pyrazole-1-acetamide was synthesized from 15 g of ethyl 4,5-diphenyl-1H-pyrazole-1-acetate, 9.2 g of N-(2-aminoethyl)piperidine, and 62 mL of diisopropylethylamine. The work up did not require extraction, as the product crystallized from the cooled reaction mixture. It was recrystallized very slowly from 250 mL of 1:3 THF-ether, mp 95°-97° C.

EXAMPLE 19

4,5-Diphenyl-N-[3-(1-pyrrolidinyl)propyl]-1H-pyrazole-1-acetamide

By a procedure substantially similar to that of Example 14, 5.52 g of 4,5-diphenyl-N-[3-(1-pyrrolidinyl)-propyl1-1H-pyrazole-1-acetamide, mp 75°-79° C., was prepared from 15 g of ethyl 4,5-diphenyl-1H-pyrazole-1-acetate and 60 mL of N-(3-aminopropyl)pyrrolidine.

EXAMPLE 20

4,5-Diphenyl-N-[2-(1-pyrrolidinyl)ethyl]-1H-pyrazole-1-acetamide

By a procedure substantially similar to that of Example 18, 6.67 g of 4,5-diphenyl-N-2-(1-pyrrolidinyl)ethyl-]1H-pyrazole-1-acetamide, mp 80°-84° C., was prepared from 15 g (0.049 mol) of ethyl 4,5-diphenyl-1H-pyrazole-1-acetate of Example 1, 9 mL (0.072 mol) of N-(2-aminoethyl)pyrrolidine and 62 mL (0.36 mol) of diisopropylethylamine.

EXAMPLE 21

4,5-Diphenyl-N-[3-(1-piperidinyl)propyl]-1H-pyrazole-1-acetamide hemihydrate A mixture of 15 g (0.049 mol) of ethyl 4,5-diphenyl-1H-pyrazole-1-acetate of Example 1, 10.2 g (0.02 mol) of 3-aminopropylpiperidine, and 62 mL of diisopropylethylamine was stirred on a steam bath under nitrogen for 18 hours. The excess amine was stripped in vacuo. The residue was taken up in about 300 mL of ether and washed twice with water. The product was extracted into 150 mL of cold water containing 18 mL of 10% hydrochloric acid. The water layer was washed two times with ether, treated with decolorizing carbon, filtered, chilled and made basic with solid sodium carbonate. The product was extracted into methylene dichloride, dried over sodium sulfate, filtered, and stripped to 14.7 g of solid residue. The residue was triturated in water, filtered and dried to yield 12.36 g of 4,5-diphenyl-N-[3-(1-piperdinyl)propyl]-1H-pyrazole-1-acetamide hemihydrate, mp 81°-85° C.

EXAMPLE 22

N-[3-(Diethylamino)propyl]-4,5-bis(4-fluorophenyl)-1H-pyrazole-1-acetamide

By a procedure substantially similar to that of Example 14, 8 g (0.023 mol) of ethyl 4,5-bis(4-fluorophenyl)-1-H-pyrazole-1-acetate of Example 3 and 34.3 mL (0.22 mol) of diethylaminopropylamine were reacted to produce 4.45 g of N-[3-(diethylamino)propyl]-4-5-bis(4-fluorophenyl)-1H-pyrazole-1-acetamide. The solid product after trituration in water collapsed to a non-crystalline, white, waxy solid upon drying.

EXAMPLE 23

N-[3-(Diethylamino)propyl]-N-methyl-4,5-diphenyl-1H-pyrazole-1-acetamide (E)-2-butenedioate (1:1)

A mixture of 28.7 g (0.09 mol) of ethyl 4,5-diphenyl-1H-pyrazole-1-acetate of Example 1, 19.7 g (0.13 mol) of diethylaminopropylmethylamine, and 94 mL (0.54 mol) of diisopropylethylamine was refluxed under nitrogen for seven days. The reaction was stripped and applied to a silica gel column using dichloromethane. Impurities were eluted with dichloromethane followed by 1.25% isopropylamine in dichloromethane. The product was eluated with 1.25% isopropylamine in chloroform. The 8 g of product was dissolved in 40 mL of warm acetone and treated with 2.3 g of fumaric acid. Upon cooling, there was obtained 9.87 g of N-[3-(diethylamino)-propyl]-N-methyl-4,5-diphenyl-1H-pyrazole-1-acetamide (E)-2-butenedioate (1:1), mp 139°–141° C.

EXAMPLE 24

N-[3-[bis(1-methylethyl)amino]propyl]-4,5-diphenyl-1H-pyrazole-1-acetamide

By a procedure substantially similar to that of Example 15, 2.49 g of N-[3-[bis(1-methylethyl)amino]propyl]-4,5-diphenyl-1H-pyrazole-1-acetamide, mp 83°–84° C., was synthesized from 12 g (0.039 mol) of ethyl 4,5-diphenyl-1H-pyrazole-1-acetate, 6.2 g (0.039 mol) of diisopropylaminopropylamine, and 35 mL of diisopropylethylamine.

EXAMPLE 25

N-[3-(Diethylamino)-2-hydroxypropyl]-4,5-diphenyl-1H-pyrazole-1-acetamide

By a procedure substantially similar to that of Example 15, 8.9 g of N-[3-(diethylamino)-2-hydroxypropyl]-4,5-diphenyl-1H-pyrazole-1-acetamide, mp 70°–72° C., was synthesized from 15 g of (0.049 mol) of ethyl 4,5-diphenyl-1H-pyrazole-1-acetate, 10 g (0.69 mol) of 1-amino-3-diethylamino-2-propanol, and 57 mL of diisopropylethylamine.

EXAMPLE 26

N-[3-(Dimethylamino)propyl]-3,4-diphenyl-1H-pyrazole-1-acetamide (E)-2-butenedioate (1:1)

A mixture of 8.35 g (0.027 mol) of ethyl 3,4-diphenyl-1H-pyrazole-1-acetate of Example 2 and 33.4 mL (0.26 mol) of dimethylaminopropylamine was stirred on a steam bath under nitrogen for 18 hours. The reaction was stripped to dryness, the residue dissolved in dichloromethane, washed twice with water and once with saturated sodium chloride solution. The product was extracted into about 100 mL of cold water containing about 12 mL of 10% HCl. The water layer was made basic with solid sodium carbonate and the product extracted into methylene dichloride, dried over sodium sulfate and stripped. The product was purified by chromatography on silica gel eluting with 5% triethylamine in chloroform. The purified product was crystallized from acetone as the fumurate salt and was recrystallized from ethanol to yield 4 47 g of N-[3-(dimethylamino)propyl]-3,4-diphenyl-1H-pyrazole-1-acetamide (E)-2-butanedioate (1:1), mp 163°–168° C.

EXAMPLE 27

N-[3-(Diethylamino)propyl]-3,4-diphenyl-1H-pyrazole-1-acetamide

By a procedure substantially similar to that of Example 26, omitting the formation of the fumarate salt, 9 g of N-[3-(diethylamino)propyl]-3,4-diphenyl-1H-pyrazole-1-acetamide was prepared from 10 g (0.033 mol) of ethyl 3,4-diphenyl-1H-pyrazole-1-acetate and 50 mL (0.32 mol) of diethylaminopropylamine. The product was an oil.

EXAMPLE 28

3,4-Diphenyl-N-[2-(1-piperidinyl)ethyl-]1H-pyrazole-1-acetamide

By a procedure substantially similar to that of Example 18, 14.0 g of 3,4-diphenyl-N-[2-(1-piperidinyl)ethyl]1H-pyrazole-1-acetamide was prepared from 16.4 g (0.054 mol) of ethyl 3,4-diphenyl-1H-pyrazole-1-acetate, 10 g (0.07 mol) of 2-aminoethylpiperidine, and 65 mL (0.37 mol) of diisopropylethylamine. The product was not recrystallized but was triturated in ether, mp 120°–124° C. A second polymorph of mp 142°–144° C. may be obtained recrystallizing from ethyl acetate.

EXAMPLE 29

3,4-Diphenyl-N-[3-(1-piperidinyl)propyl]-1H-pyrazole-1-acetamide (E)-2-butenedioate (1:1)

By a procedure substantially similar to that of Example 26, 8.56 g of 3,4-diphenyl-N-[3-(1-piperidinyl)propyl]-1H-pyrazole-1-acetamide (E)-2-butanedioate (1:1), mp 179°–180° C., was prepared from 20 g (0.065 mol) of ethyl 3,4-diphenyl-1H-pyrazole-1-acetate, 13.7 g (0.096 mol) of 3-aminopropylpiperidine, and 78 mL (0.45 mol) of diisopropylethylamine.

EXAMPLE 30

N-[2-(Diethylamino)ethyl]-3,4-diphenyl-1H-pyrazole-1-acetamide

A mixture of 10 g (0.033 mol) of ethyl 3,4-diphenyl-1H-pyrazole-1-acetate, 6.9 mL (0.049 mol) of diethylaminoethylamine and 39 mL of diisopropylethylamine was stirred on a steam bath under nitrogen for 18 hours. The reaction was stripped, the residue taken up in about 300 mL of ether and washed twice with water. The ether layer was extracted twice with a total of 150 mL of cold water containing 20 mL of 10% HCl. The combined water extracts were washed once with ether, cooled, made basic with solid sodium carbonate, extracted several times with methylene dichloride, dried over sodium sulphate, treated with decolorizing carbon, filtered and stripped. The oily red residue was crystallized from ether to yield 6.86 g of N-[2-(diethylamino)ethyl]-3,4-diphenyl-1H-pyrazole-1-acetamide, mp 80°–83° C.

EXAMPLE 31

N-(3-Aminopropyl)-4,5-diphenyl-1H-pyrazole-1-acetamide (1:4) hydrate

A mixture of 7.96 g (0.026 mol) of ethyl 3,4-diphenyl-1H-pyrazole-1-acetate and 19.2 g (0.26 mol) of 1,3-diaminopropane in 13 mL of ethanol was stirred at 84°–87° C. for 3 hours and the solvent removed in vacuo. The resulting solid was chromatographed on 34 g of silica gel eluting with 1% isopropylamine in chloroform and a gradient from 0–30% methanol. The impurities came off at 2-4% methanol followed by 6.95 g of pure product. It was crystallized three times from isopropyl acetate to yield 6 09 g of N-(3-aminopropyl)-4,5-diphenyl-1H-pyrazole-1-acetamide (1:4) hydrate, mp 119°-120° C.

EXAMPLE 32

N-(3-Hydroxpropyl)-4,5-diphenyl-1H-pyrazole-1-acetamide

A mixture of 1.47 g (4.8 mmol) of ethyl 4,5-diphenyl-1H-pyrazole-1-acetate of Example 1, 0.72 g (9.6 mmol) of 3-amino-1-propanol and 0.024 g (0.24 mmol) of triethylamine was stirred at 100° C. for two hours. Five mL of ethanol was added and the solution was poured into 20 mL of water and allowed to stand 18 hours at 5° C. to crystallize. The product was filtered off, air-dried and recrystallized from 25 mL of ethyl acetate to yield 1.47 g of N-(3-hydroxypropyl)-4,5-diphenyl-1H-pyrazole-1-acetamide, mp 138°-139° C.

EXAMPLE 33

4,5-Diphenyl-N-[3-(ethylamino)propyl]-1H-pyrazole-1-acetamide hydrochloride

A. A solution of 10 g (0.03 mol) of 4,5-diphenyl N-(3-hydroxypropyl)-1H-pyrazole-1-acetamide of Example 32 in 50 mL of pyridine was stirred at 0°-5° C. and 5.2 mL (0.066 mol) of methanesulfonyl chloride was added dropwise over 30 minutes. The reaction was filtered free of pyridine hydrochloride and added dropwise rapidly to 40 mL of ethylamine in 50 mL of pyridine at 0°-5° C. The reaction was heated 30 minutes on a steam bath, stripped in vacuo, dissolved in 100 mL of water, washed once with ethyl acetate, made strongly basic with aqueous KOH, extracted into ethyl acetate, dried and stripped to 9.9 g of free base which was a yellow oil. The oil was treated with 75 mL of 5N HCl in ethanol and 5 g of product was filtered off. The mother liquor was treated with about 75 mL of ether and a second crop of product obtained. The total yield of 4,5-diphenyl-N-[3-(ethylamino)propyl]-1H-pyrazole-1-acetamide hydrochloride was 6.5 g, m.p. 125°-137° C.

B. The dihydrochloride salt was prepared by dissolving 12 parts of the free base in 12 parts of ethanol, adding 2 equivalents (about 12 parts by volume) of 5 NHCl in ethanol, 1 part of water and 5 parts of ether. The resulting solid was filtered and recrystallized from isopropyl alcohol to yield 58% of the dihydrochloride salt, mp 166°-174° C.

C. The fumarate salt was prepared by dissolving one part of the free base in 6 parts of isopropyl alcohol, adding one equivalent of fumaric acid, heating to complete solution, cooling and filtering off the fumarate monohydrate, mp 127°-129° C. in 86% yield.

EXAMPLE 34

N-[3-(Diethylamino)propyl]-4-(4-methoxyphenyl)-5-phenyl-1H-pyrazole-1-acetamide

A solution of 7.5 g (0.022 mol) of ethyl 4-(4-methoxyphenyl)-5-phenyl-1H-pyrazole-1-acetate of example 4 in 35 mL of diethylaminopropylamine was stirred on a steam bath under nitrogen for 14 hours. The diethylaminopropylamine was removed in vacuo and the residue taken up in 200 mL of ethyl acetate. The ethyl acetate solution was washed twice with water, once with brine, and dried over sodium sulfate. The solvent was removed in vacuo and the residue was distilled in a Kugelrohr at 250° C./0.1 mm to yield 6.39 g of N-[3-(diethylamino)propyl]-4-(4-methoxyphenyl)-5-phenyl-1H-pyrazole-1-acetamide as a clear viscous amber oil.

EXAMPLE 35

N-[3-(Diethylamino)propyl]-4-(4-hydroxyphenyl)-5-phenyl-1H-pyrazole-1-acetamide

A solution of 14 g (00.33 mol) of N-[3-(diethylamino)propyl]-4-(4-methoxyphenyl)-5-phenyl-1H-pyrazole-1-acetamide of example 34 and 0.16 mol of the sodium salt of 1 propanethiol in 375 mL of DMF was heated at 155°-160° C. for 2 hours. The reaction was chilled and the excess thioproxide was neutralized with ethanolic HCl. The DMF solution was stripped under vacuum at 30°, dissolved in methylene dichloride, and washed with aqueous sodium carbonate, then water, and finally brine. The methylene chloride was dried over sodium sulfate and the solvent removed in vacuo to yield 13.4 g of gummy product. Seven grams of the gummy product was chromatographed on a silica gel column eluted with methanol/isopropylamine/chloroform (2:3:95) to yield 5.1 g of purified product. The residue was taken up in isopropyl acetate, washed twice with water, washed once with brine, and dried over sodium sulfate. The isopropyl acetate was evaporated in vacuo, but removal of the last traces of isopropyl acetate required extensive drying under high vacuum to yield 2.5 g of product as a glass.

EXAMPLE 36

N-[3-(Diethylamino)propyl]-5-(4-hydroxyphenyl)-4-phenyl-1H-pyrazole-1-acetamide

A solution of 10 g (0.031 mol) of ethyl 5-(4-hydroxyphenyl)-4-phenyl-1H-pyrazole-1-acetate of example 5 in 48 mL of diethylaminopropylamine was stirred on a steam bath under nitrogen for 14 hours. The excess amine was removed in vacuo at 80° C., the residue dissolved in ethyl acetate, washed twice with water, once with brine and dried over sodium sulfate. They ethyl acetate was stripped to yield 12 g of a dark oil which was triturated in hot cyclohexane several times. The insoluble residue was combined with a small amount of a mixture of oil and crystals, which had separated from the cyclohexane on cooling, and recrystallized from ethyl acetate to yield 6.6 g of product, mp 110°-113° C.

EXAMPLE 37

4,5-Diphenyl-N-[3-(2-methyl-1-piperidinyl)propyl]-1H-pyrazole-1-acetamide hemihydrate A solution of 15 g (0.049 mol) of ethyl 4,5-diphenyl-1H-pyrazole-1-acetate of example 1 in 17 mL (0.098 mol) of 1-(3-aminopropyl)-2-pipecoline was stirred on a steam bath for five hours. The solution was distributed between ether and water, the layers separated, and the ether layer washed several times with water. The ether solution was dried over magnesium sulfate and stripped to about 20 g of yellow oil. The oil was triturated in cyclohexane with a seed crystal obtained from the aqueous layer upon standing. The resulting white solid was filtered off and rinsed with cyclohexane to yield 17.0 g of the hemihydrate, mp 75°-76° C.

EXAMPLE 38

N-[2-[(1,1-dimethylethyl)amino]ethyl]-4,5-diphenyl-1H-pyrazole-1-acetamide

A solution of 10.7 g (0.035 mol) of ethyl 4,5-diphenyl-pyrazole-1-acetate of example 1 in 10.9 g (0.094 mol) of 2-[(1,1-dimethylethyl)amino]ethanamine was heated with about 50 mg of sodium methoxide at about 150° C. for two hours. The excess amine was stripped off under vacuum and the residue was triturated in acetonitrile. The solid product was filtered off and recrystallized from isopropyl acetate to yield 8.8 g of white crystals, mp 115°–116° C.

EXAMPLE 39

N-[3-[(1,1-dimethylethyl)amino]propyl]-4,5-diphenyl-1H-pyrazole-1-acetamide (E)-2-butenedioate (1:1)

A solution of 9.18 g (0.03 mol) of ethyl 4,5-diphenyl-pyrazole-1-acetate of example 1 in 13.8 g (0.106 mol) of 3-[(1,1-dimethylethyl)amino]propanamine was heated to about 100° C., the lower boiling material was allowed to boil off, and the temperature was raised to 180° C. for one hour. The solution was cooled to 95° and the excess amine was removed by vacuum distillation. The residual oil was dissolved in 100 mL of acetone and treated with 3.48 g of fumaric acid. The acetone was stripped, the residue dissolved in methanol, and isopropyl alcohol was added. The solution was boiled down until the product crystallized. It was recrystallized from ethanol/acetonitrile to yield 4.88 g, mp 234°–235° C.

EXAMPLE 40

N-[3-(Diethylamino)propyl]-4-(4-fluorophenyl)-5-phenyl-1H-pyrazole-1-acetamide

A solution of 8.73 g (0.027 mol) of ethyl 4-(4-fluorophenyl)-5-phenyl-1H-pyrazole-1-acetate of example 6 in 30 mL of 3-(diethylamino)propanamine was heated at reflux for 3 hr. The excess amine was stripped under vacuum and the residue triturated in 1:1 hexane/methyl t-butyl ether. The solid was recrystallized from triethylamine to yield 8.4 g of product, mp 82°–83° C.

EXAMPLE 41

4-(4-Chlorophenyl)-N-[3-(diethylamino)propyl]-5-phenyl-1H-pyrazole-1-acetamide

By a process analogous to that of example 40, 7.35 g of 4-(4-chlorophenyl)-N-[3-(diethylamino)propyl]-5-phenyl-1H-pyrazole-1-acetamide, mp 104°–105° C. from triethylamine, was synthesized from 6.8 g (0.02 mol) of ethyl 4-(4-chlorophenyl)-5-phenyl-1H-pyrazole-1-acetate of example 9 and 25 mL of 3-(diethylamino)propanamine.

EXAMPLE 42

4-(4-Bromophenyl)-N-[4-ethylmethylamino)butyl]-5-phenyl-1H-pyrazole-1-acetamide

By a process substantially similar to that of Example 30 it is contemplated that 4-(4-bromophenyl)-N-[4-(ethylmethylamino)butyl]-5-phenyl-1H-pyrazole-1-acetamide may be synthesized from N-ethyl-N-methyl-1,4-butanediamine and ethyl 4-(4-bromophenyl)-5-phenyl-1H-pyrazole-1-acetate, which is synthesized by a process substantially similar to that of Example 1A from α-(bromophenyl)-β-oxobenzene-propanal.

EXAMPLE 43

4-(2-Chlorophenyl)-N-[3-[(1,1-dimethylethyl)amino]propyl]-5-(4-methoxyphenyl)-1H-pyrazole-1-acetamide By a process substantially similar to that of Example 33 it is contemplated that 4-(2-chlorophenyl)-N-[3-[(1,1-dimethylethyl)amino]propyl]-5-(4-methoxyphenyl)-1H-pyrazole-1-acetamide may be synthesized from tert-butylamine and N-[3-(methylsulfonyloxy)propyl]-4-(2-chlorophenyl)-5-(4-methoxyphenyl)-1H-pyrazole-1-acetamide.

EXAMPLE 44

N-[7-(Diethylamino)heptyl]-4-(3-methylphenyl)-5-phenyl-1H-pyrazole-1-acetamide

By a process substantially similar to that of Example 30 it is contemplated that N-7-(diethylamino)heptyl]-4-(3-methylphenyl)-5-phenyl-1H-pyrazole-1-acetamide may be synthesized from N,N-diethyl-1,7-heptanediamine and ethyl 4-(3-methylphenyl)-5-phenyl-1H-pyrazole-1-acetate, which is synthesized by a process substantially similar to that of Example 1B from 2-(3-methylphenyl)-1-phenylethanone.

EXAMPLE 45

N-[3-(Diethylamino)propyl]-3,4-diphenyl-α-methyl-1H-pyrazole-1-acetamide

A mixture of 27.3 g (0.085 mol) of ethyl 3,4-diphenyl-α-methyl-1H-pyrazole-1-acetamide of example 9 and 120 mL of 3-(diethylamino)propanamine was heated 5 hr on a steambath. The reaction was poured into water and extracted into ethyl acetate. The ethyl acetate layer was dried and stripped to an oil in which a solid slowly crystallized. The crystals were removed and recrystallized from cyclohexane to yield 6.2 g of N-[3-(diethylamino)propyl]-3,4-diphenyl-α-methyl-1H-pyrazole-1-acetamide, mp 87°–89° C.

EXAMPLE 46

N-[3-(Diethylamino)propyl]-4,5-diphenyl-α-methyl-1H-pyrazole-1-acetamide

By a process substantially similar to that of example 45, it is contemplated that N-[3-(diethylamino)propyl]-4,5-diphenyl-α-methyl-1H-pyrazole-1-acetamide may be synthesized from ethyl 4,5-diphenyl-α-methyl-1H-pyrazole-1-acetate of example 8 and 3-(diethylamino)propanamine.

EXAMPLE 47

N-[3-[(1,1-Dimethylethyl)amino]propyl]-α-ethyl-4-(4-methoxyphenyl)-5-phenyl-1H-pyrazole-1-acetamide By a process substantially similar to that of example 45, it is contemplated that N-[3-[(1,1-dimethylethyl)amino]propyl]-α-ethyl-4-(4-methoxyphenyl)-5-phenyl-1H-pyrazole-1-acetamide may be synthesized from ethyl α-ethyl-4-(4-methoxyphenyl)-5-phenyl-1H-pyrazole-1-acetate of example 11 and 3-(t-butylamino)propylamine.

EXAMPLE 48

N-[3-(Diethylamino)propyl]-α,α-dimethyl-4,5-diphenyl-1H-pyrazole-1-acetamide.

By a process substantially similar to that of example 45, it is contemplated that N-[3-(diethylamino)propyl]-α,α-dimethyl-4,5-diphenyl-1H-pyrazole-1-acetamide may be synthesized from ethyl α,α-dimethyl-4,5-diphenyl-1H-pyrazole-1-acetate of example 10 and 3-(diethylamino)propanamine.

EXAMPLE 49

N-[3-(Diethylamino)propyl]-4,5-diphenyl-1H-pyrazole-1-ethanamine (E)-2-butenedioate (1:2)

A solution of 11.5 g (0.029 mol) of N-[3-(diethylamino)propyl]-4,5-diphenyl-1H-pyrazole-1-ethanamine of example 12 in 160 mL of THF was added dropwise with stirring at 0° C. under nitrogen to 240 mL of a 1M THF solution of diborane (0.024 mol). The reaction was slowly heated to reflux and allowed to reflux 18 hr. The solvent and excess diborane were stripped off in vacuo, and the residue was treated with 400 mL of 6N HCl, cautiously at first, then with heating on steambath for 1 hr. The solution was cooled, made basic with NaOH, and extracted into methylene chloride; the methylene chloride solution was dried over $MgSO_4$ and stripped to a dark oil. The oil was dissolved in hot ethanol and a solution of 2 equivalents of fumaric acid in hot ethanol was added. The solution was chilled and 8.7 g of N-[3-(diethylamino)propyl]-4,5-diphenyl-1H-pyrazole-1-ethanamine (E)-2-butenedioate (1:2), mp 95°–100° C., was obtained by filtration.

EXAMPLE 50

N-[3[(1,1-Dimethylethyl)amino]propyl]-α-ethyl-4-(4-methoxyphenyl)-5-phenyl-1H-pyrazole-1-ethanamine By a process substantially similar to that of example 49, it is contemplated that N-[3-[(1,1-dimethylethyl)amino]propyl]-α-ethyl-4-(4-methoxyphenyl)-5-phenyl-1H-pyrazole-1-ethanamine may be synthesized from N-[3-[(1,1-dimethylethyl)amino]propyl]-α-ethyl-4-(4-methoxyphenyl)-5-phenyl-1H-pyrazole-1-acetamide of example 47.

EXAMPLE 51

N-[3-(Diethylamino)propyl]-5-(4-hydroxyphenyl)-4-phenyl-1H-pyrazole-1-ethanamine.

By a process substantially similar to that of example 49, it is contemplated that N-[3-(diethylamino)propyl]-5-(4-hydroxyphenyl)-4-phenyl-1H-pyrazole-1-ethanamine may be synthesized from N-[3-(diethylamino)propyl]-5-(4-hydroxyphenyl)-4-phenyl-1H-pyrazole-1-acetamide of example 36.

EXAMPLE 52

N-[3-(Diethylamino)propyl]-4,5-bis(4-fluorophenyl)-1H-pyrazole-1-ethanamine

By a process substantially similar to that of example 49, it is contemplated that N-[3-(diethylamino)propyl]-4,5-bis(4-fluorophenyl)-1H-pyrazole-1-ethanamine may be synthesized from N-[3-(diethylamino)propyl]-4,5-bis(4-fluorophenyl)-1H-pyrazole-1-acetamide of example 22.

The compounds of examples 1 to 44 are starting materials from which compounds of the invention may be prepared utilizing the procedures of examples 45 and 49.

The antiarrhythmic activity of compounds of the invention was demonstrated by the following procedure.

Duncan Hartley guinea pigs (600–900 grams) of either sex were anesthetized with urethane (1.4 g/kg, i.p.) and supplemented as needed. An intravenous route for drug administration was established using microbore tubing inserted into the jugular vein. The induction of arrhythmias by aconitine hydrochloride (34 g/kg) was evaluated in control guinea pigs given 1 cc saline as an intravenous bolus 10 minutes prior to aconitine challenge.

Compounds to be tested were administered intravenously 10 minutes prior to aconitine challenge at an initial dosage of 30 mg/kg. This dosage was reduced in subsequent animals if severe cardiac rhythm disturbances persisted beyond two minutes after injection in the first guinea pig tested. All drugs were tested at the maximally tolerated dose (identified by the lack of arrhythmias in the EKG prior to aconitine challenge). Compounds were administered in saline as 1 cc bolus injections (n=5–9).

Time intervals between aconitine injection and the appearance of arrhythmias were determined. Specifically noted was the time until the onset of (i) the first premature ventricular contraction (PVC); (ii) the first sustained run of ventricular tachycardia consisting of 10 or more ventricular beats (VTACH); and (iii) the time until the appearance of ventricular fibrillation lasting longer than 15 seconds (VFIB). The average time and standard error of the mean until the appearance of these arrhythmias were calculated for each treatment group and compared to concurrent controls using a one-way analysis of variance. Activity was defined as a statistically significant delay in the onset of PVC, VTACH and VFIB time course compared to control values.

The following table summarizes the results obtained from the testing of representative compounds of the invention.

| Example No. | Minutes to | | |
|---|---|---|---|
| | PVC | VTACH | VFIB |
| Control | 0.7–1.0 | 1.0–2.0 | 3.7–7.9 |
| 45 | 13.5* | 22.7 | 47.9 |
| 49 | 20.7* | 48.6 | 57.3 |

*not statistically significant

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

We claim:

1. A compound of formula

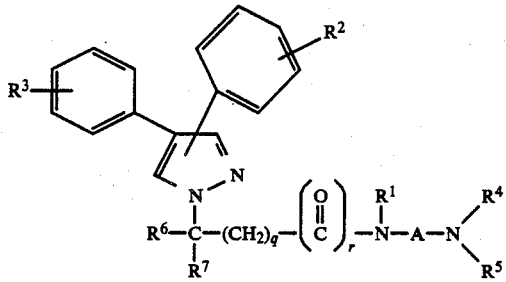

or acid addition salt or solvate thereof wherein $R^1$ is hydrogen or lower-alkyl; $R^2$ and $R^3$ are independently hydrogen, hydroxy, lower-alkyl, lower-alkoxy, or halo; $R^4$ and $R^5$ are independently hydrogen or lower-alkyl, or $R^4$ and $R^5$ together form a straight or branched alkylene chain of four to six carbon atoms; $R^6$ and $R^7$ are independently hydrogen or straight-chain lower-alkyl; r is zero; q is one; and A is $CH_2CH(OH)CH_2$ or $(CH_2)_n$ wherein n is an integer from two to eight.

2. A compound according to claim 1 wherein $R^1$ is hydrogen.

3. A compound according to claim 2 wherein n is two or three.

4. A compound according to claim 3 wherein $R^6$ and $R^7$ are both hydrogen, r is zero, and having the formula

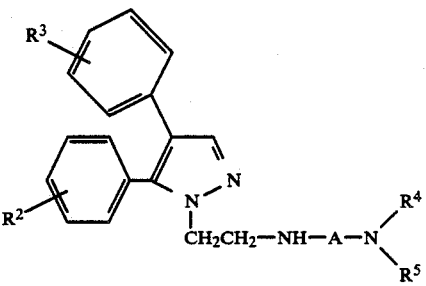

5. N-[3-(Diethylamino)propyl]-4,5-diphenyl-1H-pyrazole-1-ethanamine or an acid addition salt or solvate thereof according to claim 4.

6. A composition for treating cardiac arrhythmias comprising an amount of a compound according to claim 1 effective to treat cardiac arrhythmias together with one or more pharmaceutically acceptable excipients or diluents.

7. A composition for treating cardiac arrhythmias comprising an amount of a compound according to claim 4 effective to treat cardiac arrhythmias together with one or more pharmaceutically acceptable excipients or diluents.

8. A composition for treating cardiac arrhythmias comprising an amount of N-[3-(diethylamino)propyl]-4,5-diphenyl-1H-pyrazole-1-ethanamine or pharmaceutically acceptable acid addition salt or solvate thereof according to claim 5 effective to treat cardiac arrhythmias together with one or more pharmaceutically acceptable excipients or diluents.

9. A method for treating cardiac arrhythmias in a susceptible subject which comprises the step of administering an amount of a compound according to claim 1 effective to treat cardiac arrhythmias.

10. A method for treating cardiac arrhythmias in a susceptible subject which comprises the step of administering an amount of a compound according to claim 4 effective to treat cardiac arrhythmias.

11. A method for treating cardiac arrhythmias in a susceptible subject which comprises the step of administering an amount of N-[3-(diethylamino)propyl]-4,5-diphenyl-1H-pyrazole-1-ethanamine or pharmaceutically acceptable acid addition salt thereof according to claim 5 effective to treat cardiac arrhythmmias.

* * * * *

UNITED STATES PATENT AND TRADEMARK OFFICE
CERTIFICATE OF CORRECTION

PATENT NO. : 4,916,150

DATED : April 10, 1990

INVENTOR(S) : Denis M. Bailey and Ronald G. Powles

It is certified that error appears in the above-identified patent and that said Letters Patent is hereby corrected as shown below:

Abstract, line 1): "N-[alkylamino)" should read --- N[(alkylamino) ---.

Column 1, line 60 "mide) (example 160)" should read --- mide (example 160) ---.

Column 2, line 45: "adminsitering" should read --- administering ---.

Column 9, line 18: "substantilly" should read --- substantially ---.

Column 10, line 26): "isopropyl and" should read --- isopropyl alcohol and ---.

Column 10, line 38: "1-H" should read --- 1H ---.

Column 10, line 49: "resulting was" should read --- resulting solid was ---.

Column 12, line 5: "piperdinly" should read --- piperdinyl ---.

Column 12, line 65): "1-H" should read --- 1H ---.

Column 14, line 25: "obtained recrystallizing" should read --- obtained by recrystallizing ---.

Column 16, line 14: "thioproxide" should read --- thiopropoxide ---.

Column 1, line 18: "antiarrythmic" should read --- antiarrhythmic ---.

Column 4, line 5: "teated" should read --- treated ---.

Column 5, line 31: "-aminoalkanol" should read --- ω-aminoalkanol ---.

Column 5, line 34: " -hydroxyalkyl" should read --- ω-hydroxyalkyl ---.

UNITED STATES PATENT AND TRADEMARK OFFICE
CERTIFICATE OF CORRECTION

PATENT NO. : 4,916,150

DATED : April 10, 1990

INVENTOR(S) : Denis M. Bailey and Ronald G. Powles

Page 2 of 2

It is certified that error appears in the above-identified patent and that said Letters Patent is hereby corrected as shown below:

Column 7, line 66: "example 1B 11g" should be --- example 1B, 11g ---.

Column 8, line 11: hydrazino acetate" should read --- hydrazinoacetate ---.

Column 9, line 25: "Ethyl-4-(4-" should read --- Ethyl-α-ethyl 4-(4 ---.

Column 9, line 28: "ethyl-4-(4-" should read --- ethyl-α-ethyl 4-(4- ---.

Column 11, line 60: ")ethyl1-4" should read --- )ethyl]-4 ---.

Column 12, line 23: "propyl1-1H" should read --- propyl]-1H ---.

Column 12, line 32: "ethyl-]" should read --- ethyl]- ---.

Column 13, line 66: "4 47" should read --- 4.47 ---.

Column 14, line 15: "ethyl-]" should read --- ethyl]- ---.

Column 15, line 3: "6 09 g" should read --- 6.09 g ---.

Column 16, line 43: "They" should read --- The ---.

Column 22, line 47: "arrhythmmias" should read --- arrhythmias ---.

Signed and Sealed this

Fourth Day of August, 1992

Attest:

DOUGLAS B. COMER

*Attesting Officer*

*Acting Commissioner of Patents and Trademarks*